United States Patent [19]

Nylen et al.

[11] 4,266,021
[45] May 5, 1981

[54] METHOD AND APPARATUS FOR THE MEASUREMENT OF THE CONCENTRATION OF A COMPOUND IN A LIQUID MEDIUM

[75] Inventors: Ulf T. G. Nylen; Lars-Göran Olsson; Bengt G. Paulsson; Lars A. G. Qvarnström, all of Lund; Rolf H. L. Wichers, Södra Sandby, all of Sweden

[73] Assignee: Gambro AB, Sweden

[21] Appl. No.: 968,202

[22] Filed: Dec. 11, 1978

[30] Foreign Application Priority Data

Dec. 16, 1977 [SE] Sweden ............... 7714335

[51] Int. Cl.³ .................. C12M 1/34; C12Q 1/54; G01N 31/14
[52] U.S. Cl. .................... 435/14; 435/4; 435/291; 23/230 B; 422/81
[58] Field of Search ............. 210/22 C, 96 M, 188, 210/321 A; 435/4, 14, 287, 288, 289, 291; 422/68, 81, 82, 101

[56] References Cited

U.S. PATENT DOCUMENTS

| | | | |
|---|---|---|---|
| 3,109,714 | 11/1963 | Skeggs | 422/82 |
| 3,398,091 | 8/1968 | Greatorex | 210/188 |
| 3,937,615 | 2/1976 | Clack et al. | 435/14 |
| 4,060,485 | 11/1977 | Enton | 210/96 M |
| 4,123,353 | 10/1978 | Hakansson et al. | 210/22 C |
| 4,153,513 | 5/1979 | Edelmann et al. | 435/14 |
| 4,170,520 | 10/1979 | Weaver | 435/291 |
| 4,221,567 | 9/1980 | Clark et al. | 23/230 B |
| 4,229,542 | 10/1980 | Nylen et al. | 435/291 |

FOREIGN PATENT DOCUMENTS

318425 12/1969 Sweden.
340190 11/1971 Sweden.
396819 10/1977 Sweden.

Primary Examiner—Thomas G. Wiseman
Attorney, Agent, or Firm—Lerner, David, Littenberg & Samuel

[57] ABSTRACT

A method and apparatus is provided for measuring the content of a compound in a liquid medium, and which is particularly useful for measuring the concentration of a low molecular weight compound in a complex medium in which there is provided a dialyzer in contact with the complex fluid medium and through which dialysis fluid is conducted to receive by diffusion a portion of the low molecular weight compound to produce a dialysate. The dialysate with the low molecular weight commpound to be examined is first conducted through a venting device for removal of gaseous particles therefrom before conduction through a reaction chamber containing enzymes for promoting the conversion of the low molecular weight compound in the dialysate into a converted reaction product. The dialysate is then conducted from the reaction chamber to a measuring unit for measuring the concentration of the converted reaction product in the dialysate conducted from the reaction chamber, the concentration of the converted reaction product being representative of the content of the low molecular weight compound in the complex fluid medium.

44 Claims, 4 Drawing Figures

METHOD AND APPARATUS FOR THE MEASUREMENT OF THE CONCENTRATION OF A COMPOUND IN A LIQUID MEDIUM

BACKGROUND OF THE INVENTION

The present invention relates generally to a method and apparatus for measuring the concentration of a compound in a liquid medium in which the medium being examined is passed through an enzyme bed or the like for the transformation of the compound into a converted reaction product, the concentration of which can then be easily measured in a measuring unit. The enzyme bed can either serve to form a converted reaction product which is then measured after being conducted from the reaction chamber or can serve to remove the reaction product therefrom, the absence of which is then measured by the measuring unit. In particular, the method and apparatus of the present invention are particularly useful for measuring the content of a low molecular weight compound, such as for example glucose in a complex medium such as for example blood.

In measuring the concentration of a low molecular weight compound in a complex medium, such as for example blood, a dialyzer is employed in contact with the complex medium and through which dialysis fluid is conducted to receive by diffusion a portion of the low molecular weight compound to produce a dialysate. This dialysate is then transmitted to a reaction chamber comprised of an enzyme bed or the like which serves to promote the conversion of the low molecular weight compound into a converted reaction product and then to a measuring unit for measuring the content of a converted reaction product in the fluid conducted from the reaction chamber. This measurement of the concentration of the converted reaction product is representative of the concentration of the low molecular weight compound in the complex medium. Such a measurement can, in turn, be used for controlling the treatment of the complex medium, for example, by supplying insulin and/or glucose to the blood of the patient being examined.

However, during such a process, there is a possibility that gaseous products carried by the dialysate may adversely affect the enzymes in the reaction chamber, the conversion of the low molecular weight compound into the converted reaction product and/or the measurement of the content of the converted reaction product. For example, the pentration of air into the enzyme bed may adversely affect the accuracy of the measurement of the concentration of the low molecular weight compound in the complex medium which is particularly disadvantageous where such measurement is being used to control the supply of insulin and/or glucose to a patient under examination.

Accordingly, it is an object of the present invention to provide a method and apparatus for overcoming these disadvantages of the prior art. Specifically, it is an object of the present invention to provide a method and apparatus for obtaining a reliable measurement of the concentration of a compound in a liquid medium, and in particular, for obtaining the measurement of a concentration of the low molecular weight compound in a complex medium.

SUMMARY OF THE INVENTION

In accordance with the principles of the present invention, a method and apparatus is provided for measuring the concentration of a compound in a liquid medium, which is particularly useful for measuring the concentration of a low molecular weight compound in a complex medium. The method of the present invention comprises first removing gaseous particles from the liquid medium containing the compound whose concentration is to be measured and then conducting the liquid medium in which the gaseous particles have been removed through a reaction chamber containing enzymes. The enzymes serve to promote the conversion of the compound whose concentration is to be measured into a converted reaction product. The liquid medium is then conducted from the reaction chamber to a measuring unit for measuring the concentration of the converted reaction product in the liquid medium, the concentration of this converted reaction product being representative of the concentration of the compound in the liquid medium.

According to the apparatus of the present invention, there is provided a fluid conduit through which the liquid medium is conducted to a gas removing means for removing gaseous particles from the liquid medium when the liquid medium passes therethrough. A reaction chamber is coupled downstream of the gas removal means for receiving the liquid medium after it is passed through the gas removal means. The reaction chamber contains enzymes for promoting the conversion of the compound whose concentration is to be measured into a converted reaction product. A measuring means for measuring the concentration of the converted reaction product in the liquid medium is coupled downstream of the reaction chamber to receive the liquid medium after passage through the reaction chamber.

When the method and apparatus of the present invention are used for measuring the concentration of a low molecular weight compound in a complex medium, the liquid medium comprises a dialysate which is produced by supplying dialysis liquid through a dialyzer in contact with the complex medium for receiving a portion of the low molecular weight compound by diffusion in the dialyzer.

According to the preferred embodiment of the present invention, the reaction chamber is provided with an inlet through which the liquid medium is introduced and an outlet through which the liquid medium is withdrawn, the inlet being at a higher elevation than the outlet so that the liquid medium is conducted through the reaction chamber from a higher elevation to a lower elevation. In this way, the gaseous particles may advantageously be removed by placing the gas removal means at a higher elevation than the inlet to the reaction chamber.

These and further features and characteristics of the present invention will be apparent from the following detailed description in which reference is made to the enclosed drawings which illustrate the preferred embodiment of the present invention.

DESCRIPTION OF THE PREFERRED EMBODIMENT

Figure 1:
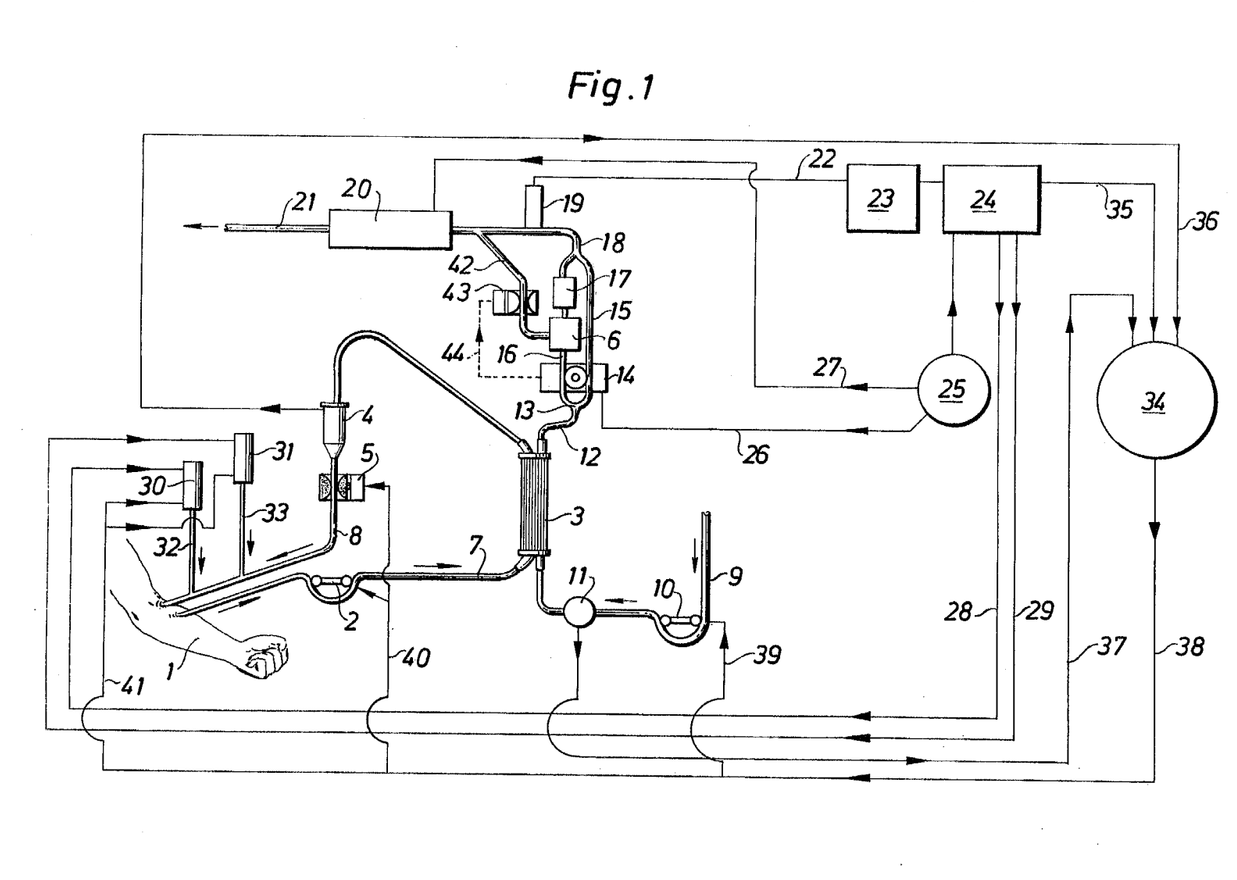
FIG. 1 schematically illustrates a substantially complete system for the analysis and control of the glucose content in the blood of a patient in which the present invention is incorporated.

FIG. 1 shows a schematic diagram of a complete system for sampling and measuring of the content of a low molecular weight compound in a complex medium in which the present invention is particularly useful. In the embodiment shown, the complex medium is blood which is withdrawn from a patient under examination and in which the low molecular weight compound, for example glucose, is mixed with high molecular weight compounds and/or other low molecular weight compounds. As a result of the reliable measurement obtained with use of the present invention, the system shown in FIG. 1 may thus be applied for controlling the glucose content in the blood of the patient, such as for example by controlling the supply of insulin and/or glucose.

The method and apparatus in accordance with the present invention are principally intended for use in connection with such a system for analyzing and monitoring as shown in FIG. 1, and will therefore be described with reference thereto. However, it will be evident to those versed in the art that the invention can also be applied more generally. For example, the method and apparatus of the present invention may be employed to examine many other complex mediums other than blood, and in fact can be employed in any system for the measurement of a concentration of a compound in a liquid medium in which the medium being examined is passed through an enzyme bed or the like for the transformation of the compound being tested into a converted reaction product, the formation and/or removal of which can be easily measured in a subsequent measuring unit. However, in the following, the description is restricted only to blood.

In the embodiment shown, the blood is withdrawn from a patient 1 and is pumped by means of a pump 2 through a dialyzer 3 and back to the patient via an air trap 4 and tube clamp 5. The blood is conducted via an arterial line 7 and a venous line 8, respectively. Dialysis liquid is supplied to the dialyzer 3 through a line 9 via pump 10 and a pressure transmitter 11. The dialyzer 3 serves to dialyize the complex medium to separate a certain portion of the compound being tested, which in the particular embodiment shown consists of a low molecular weight compound, for example glucose. The dialysis fluid supplied to the dialyzer 3 receives by diffusion this portion of the glucose to produce a dialysate which is then conducted via a line 12 to a branching point 13.

Preferably, a dialyzer is chosen which has a substantially smaller volume on the side of the dialysis fluid then on the side of the complex medium to be examined, so that the latter is affected only insignificantly and can be returned to its source. The dialyzer 3 may be comprised, for example, of a fiber dialyzer with only one or a small number of fibers for the conducting of the dialysis fluid, while the medium to be examined is arranged to be conducted outside these fibers. Such a fiber dialyzer is described in detail in U.S. patent application Ser. No. 755,977, filed on Dec. 30, 1976, U.S. Pat. No. 4,229,542 and is therefore not described in any detail in the present patent application. In this aforementioned patent application, an analysis procedure is also described which is relevant to the method and apparatus in accordance with the present invention. With regard to technical details, such as choice of enzyme, dilution, buffers, etc., reference is made to this above-mentioned patent application which is hereby incorporated as though fully set forth herein.

From the branching point 13, the dialysate can be conducted with the help of a flow changeover device 14 either through a shunt line 15 or through a main line 16 comprising a gas removal or venting device 6 and a reaction chamber or enzyme bed 17 to a merger point 18. Thereafter the dialysate is conducted to a measuring unit, which, in the example shown, consists of a measuring electrode 19. Subsequently, the dialysate passes through a flow meter 20 to an outlet or discharge line 21.

The flow changeover device 14 serves to intermittently divert the flow of dialysate through either the shunt line 15 or the main line 16. U.S. Pat. No. 4,123,353 described such a changeover device which is particularly useful for intermittently diverting the flow of dialysate wherein the flow conduits or lines 12, 15, 16, etc., are comprised of compressible flexible tubing which may be compressed to stop the flow of fluid therethrough. This division of the dialysate into first and second partial flows one, of which is adapted to be conducted through the enzyme bed 17 and the other of which passes directly through the measuring unit, is particularly useful for providing a zero-value or reference based for the measurement to be performed by the measuring unit 19'. For example, the partial flow being directly conducted to the measuring unit will provide a zero value or reference point based on the other factors in the complex medium, as specifically noted in U.S. Pat. No. 4,123,353.

The result obtained in the measuring unit 19 is transmitted via an electric line 22 to an electometer 23 and further to a computer 24. To this computer 24 are also fed pulses from a clock 25 which also transmits pulses to the flow changeover device 14 and the flow meter 20, respectively. The latter pulses are transmitted via lines 26 and 27, respectively. The computer 24 also controls via lines 28 and 29 the pumping arrangements 30 and 31, which, for example, may supply insulin or glucose via conduit lines 32 or 33, respectively, which open directly into venous tube 8. Numeral 34 designates an alarm center which may either constitute a separate unit or form part of the computer 24. In the example shown, this alarm unit 34 is designed as a separate unit and therefore receives pulses from the computer 24 via line 35. The alarm unit 34 also receives pulses from the air trap 4 via line 36 and from the pressure transmitter 11 via line 37. The alarm unit 34 in turn gives off pulses via line 38 and the branch lines 39, 40 and 41 to the pump 10 for the dialysis fluid, the pump 2 and the tube clamp 5 for the blood, as well as to the pumps 30 and 31 for insulin and glucose, respectively. In this manner, the whole analytical procedure can be rapidly discontinued if any fault occurs.

In the foregoing, only the most important functions of the arrangement have been described. It will be understood, however, that the system described above may be modified in accordance with whatever is required in the individual case.

In the schematic illustration of FIG. 1, the gas removal or venting device 6 is shown as including a discharge line 42 which communicates directly with the discharge line 21. The line 42 serves as a discharge for the gaseous particles removed by the venting device 6 to prevent such gaseous particles from entering into the enzyme bed 17. In practice, this line 42 consists of compressible or flexible tubing or the like, similar to the lines 15 and 16. The line 42 can therefore be acted upon by means of a compression device 43 for controlling the flow of fluid therethrough.

In the preferred embodiment, the compression device 43 is controlled as a function of the changeover device 14, as indicated by the broken line 44. This is appropriately adapted so that the device 43 is opened for a short instant each time a changeover takes place by operation of the changeover device 14 to divert the flow of dialysate either through the shunt line 15 or the main line 16. In this manner, a small portion of the liquid medium in the line 16 is discharged through the venting device 6 together with any gaseous particles accumulated therein as more fully described hereinbelow with reference to FIG. 2. This accordingly ensures that the gaseous particles collected in the venting device 6 will pass through the outlet line 42 and not into the enzyme bed 17.

Figure 2:
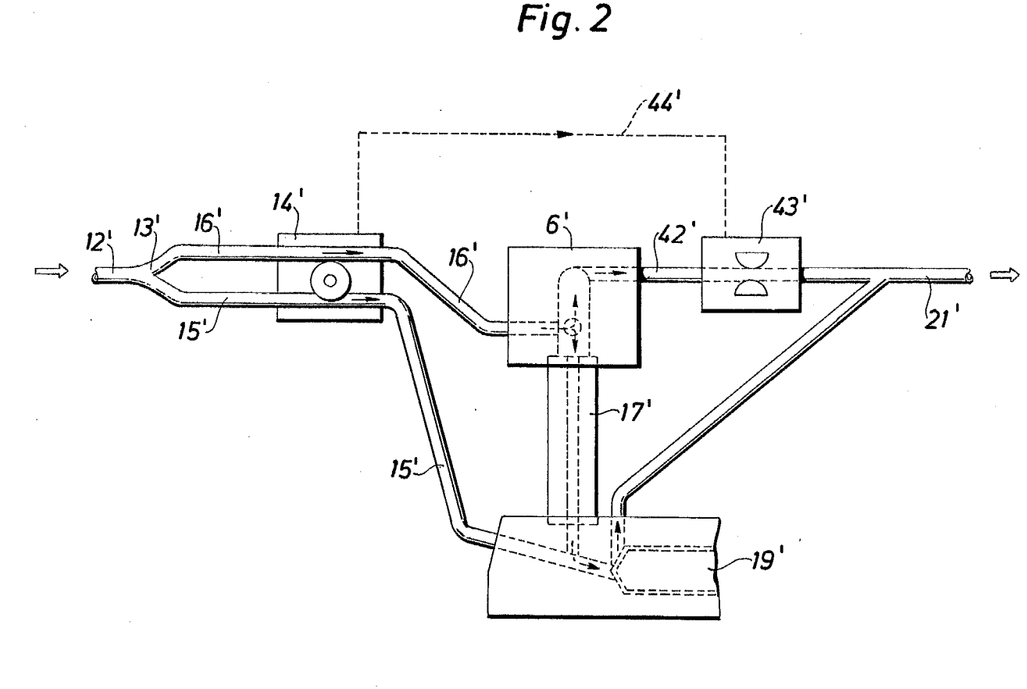
FIGS. 2, 3 and 4 illustrate schematically alternative venting arrangements which may be used in connection with the system illustrated in FIG. 1.

FIG. 2 illustrates in greater detail a preferred arrangement and orientation of the components of the apparatus used in the system of FIG. 1 for measuring the concentration of the low molecular weight compound, for example glucose, in the blood of the patient being examined. As the function corresponds substantially to that shown for the components in FIG. 1, the same reference designations have therefore been used for corresponding parts, but with the addition of a prime sign. Thus, the dialysate or other liquid medium being examined, is supplied via line 12' to branching point 13'. From there, the liquid medium to be examined is conducted either through shunt line 15' or main line 16'. The changeover between these lines takes place with the help of a changeover device 14' which serves to intermittently allow the flow of dialysate through either line 15' or line 16' by compressibly closing one of the lines while simultaneously opening the other of the lines. The shunt line 15' leads directly to the measuring electrode 19'. The main line 16' also leads to this measuring electrode 19', but in this case, via a venting device 6' and an enzyme bed 17'. The enzyme bed 17' comprises a reaction chamber containing enzymes therein for promoting the conversion of the compound to the examined into a converted reaction product in a well known manner. The converted reaction product may then pass with the liquid medium to the electrode 19' or can in fact be removed in the enzyme bed 17'. In any event, the measuring electrode 19' serves to measure the concentration of the converted reaction product after passage through the enzyme bed 17'. Depending upon the particular enzymes, and the compound being measured, the concentration of the converted reaction product measured by the electrode 19' serves as an indication or representation of the concentration of the compound being measured in the complex medium, as more fully described in the aforementioned copending application Ser. No. 755,977, U.S. Pat. No. 4,229,542.

As in the FIG. 1 representation, the venting device 6' in FIG. 2 includes a separate outlet line 42' which is adapted to be opened and shut by means of a compression device 43'. As indicated by the broken line 44', the compression device 43' is controlled as a function of the changeover device 14'. In this embodiment, the venting device 6' serves to collect and accumulate any gaseous particles, for example air, in the upper portion of the venting device 6' to remove same from the dialysate to be examined. Each time that a changeover from one partial flow to another takes place as a result of operation of the changeover device 14', the compression device 43' is opened and a portion of the dialysate is withdrawn together with any collected gaseous particles through the line 42' to ensure discharge of the collected gaseous particles. In this way, the venting is coordinated with the changeover between one partial flow and another, and thus no extra control element is required for the venting. In all the coupling positions, the dialysate is finally removed via an outlet line 21'.

Further, it is to be noted that by virtue of the arrangement shown in FIG. 2, the venting of the liquid medium to be examined is carried out at the top of the enzyme bed 17' while the flow of the liquid medium to be examined is conducted through the bed 17' substantially from the top downward. In this way, the risk of penetration of any air or other gaseous particles into the enzyme bed 17' is reduced which might otherwise adversely affect the enzymes in the bed 17', the conversion of the compound to be measured into a converted reaction product, and/or the accuracy of the measurement obtained.

Figure 3:
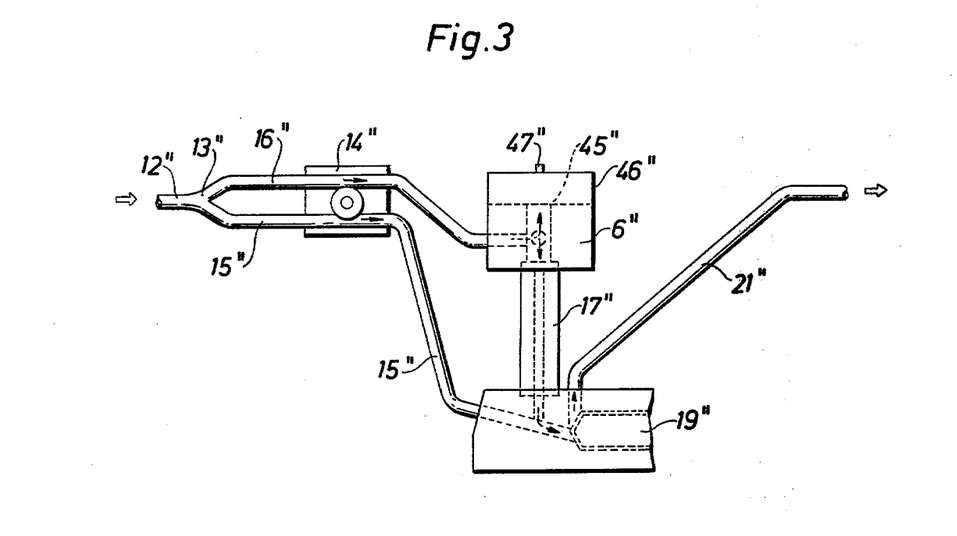

FIG. 3 shows a modification of the arrangement according to FIG. 2 which is useful in the system schematically shown in FIG. 1. Here too, the same reference designations have been used, though with the addition of a double prime sign. In the FIG. 3 embodiment, the medium to be examined is supplied via an inlet line 12" to a branching point 13" and from there through either lines 15" or 16", respectively, as controlled by the changeover device 14". The line 15" leads directly to the measuring electrode 19" while the line 16" leads to the same electrode 19", but via venting device 6" and an enzyme bed 17". In the venting device 6", the venting is achieved with the help of a liquid-tight but gas permeable membrane 45". This membrane may consist, for example, of a hydrophobic membrane with pores which are permeable for gas. Examples of such useable membranes are polypropylene, polyethylene, or Teflon, subject to their being manufactured with suitable pores. Preferably, the pores are smaller than 0.002 mm and are appropriately of an order of magnitude of 0.005 mm. The permeability for gas and liquid may be altered, if the membrane is acted upon from the outside. Accordingly, the membrane is preferably protected by a casing 46" with a vent hole 47", in the example shown.

In this construction, the dialysate to be passed through the enzyme bed 17" is conducted into the lower half of the casing 46". The gaseous particles pass upwardly through the membrane 45" while the liquid remains in the lower half of the casing 46". The gas thus removed passes through the vent hole 47' into the atmosphere or other appropriate outlet. On the other hand, the liquid with the gaseous particles removed therefrom is conducted through the enzyme bed 17", preferably arranged below the venting device 6" so that the flow of the liquid medium is substantially from top to bottom through the enzyme bed 17". The construction in accordance with FIG. 3 differs from that in accordance with FIG. 2 in that the venting takes place continuously so that no significant amount of gaseous particles or air can accumulate above the enzyme bed 17".

For the electrodes 19, 19' and 19", any known and commercially available construction may be chosen. If glucose is to be analyzed, it is possible to measure either the oxygen content or the perioxide content. Further, the electrodes may differ from one another with respect of the membrane and the potential use.

Figure 4:
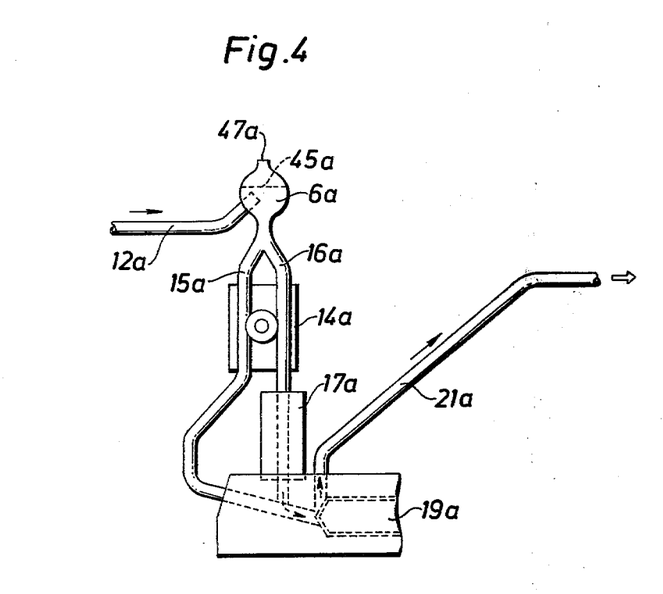

FIG. 4 shows a further emmbodiment or modification of the venting device in accordance with the present invention. This construction also functions in principle, in the same manner as those according to FIGS. 1, 2 and 3, and so the same reference designations have been used with the addition of the letter "a". Numeral 12a thus designates a line from a dialyzer or other source of liquid medium having a compound whose concentration is to be measured. The line 12a terminates in a separate venting device 6a comprising a gas permeable membrane 45a and a vent hole 47a, similar to the membrane 45" and vent hole 47" described above with reference to FIG. 3. In the FIG. 4 embodiment however, it is only after venting or the removal of the gaseous particles that the line divides into two branch lines 15a and 16a, respectively, between which a changeover can take place with the help of a flow changeover device 14a for dividing the liquid into first and second partial flows. The line 16a leads via an enzyme bed 17a to the electrode 19a. The line 15a on the other hand leads directly to the electrode 19a without passing through the enzyme bed 17a to provide a reference or zero value for comparison purposes. The dialysate examined is finally removed by means of outlet lines 21a.

It is to be noted that with both of the arrangements shown in FIGS. 3 and 4, the vent holes 47" and 47a are provided in the form of a cap with one or more small vent holes so as to prevent any touching of the membranes 45", 45a therein from outside the venting device 6", 6a which might otherwise hinder or alter the permeability of the membranes. Further, in the embodiment shown, compressible tubing is preferred for the various fluid conduits in that such tubing can be acted upon with no direct contact with the medium being examined from the outside. Further, the tubing and other parts which come into contact with the medium can be in the form of expendable or disposable components which can be simply discarded after use.

While the preferred embodiments of the present invention have been shown and described, it will be understood that such are merely illustrative and that changes may be made wihout departing from the scope of the invention as claimed.

What is claimed is:

1. A method of measuring the concentration of a compound in a liquid medium comprising the steps of:
providing a reaction chamber which contains enzymes for promoting the conversion of said compound whose concentration is to be measured into a converted reaction product when said liquid medium containing said compound whose concentration is to be measured is conducted therethrough, said reaction chamber having an inlet and an outlet, and said inlet being at an elevation above said outlet;
arranging a venting device at an elevation above said inlet of said reaction chamber and in fluid communication with said inlet of said reaction chamber, said venting device including a gas permeable membrane having pores to allow gaseous bubbles to pass therethrough, said membrane being substantially impervious to the flow of liquid therethrough;
conducting said liquid medium containing said compound whose concentration is to be measured through said venting device in contact with said gas permeable membrane for venting of gaseous bubbles through said gas permeable membrane so as to provide a liquid medium with gaseous bubbles removed therefrom;
conducting said liquid medium with said gaseous bubbles removed therefrom from said venting device to said inlet of said reaction chamber;
conducting said liquid medium with said gaseous bubbles removed therefrom from said inlet of said reaction chamber to said outlet of said reaction chamber to thereby promote conversion of said compound whose concentration is to be measured into a converted reaction product and provide a processed liquid medium; and
then conducting said processed liquid medium from said outlet of said reaction chamber to a measuring unit for measuring the concentration of said converted reaction product in said processed liquid medium, the concentration of said converted reaction product being representative of the concentration of said compound in said liquid medium.

2. The method of claim 1 further including the step of first collecting the gaseous bubbles vented through said gas permeable membrane in said venting device and then discharging said collected bubbles through an outlet conduit which is separate from said reaction chamber.

3. The method of claim 1 further including the step of continuously discharging said gaseous bubbles vented through said gas permeable membrane.

4. The method of claim 3 wherein said hydrophobic membrane is made from the group consisting of polypropylene teflon and polyethylene.

5. The method of claim 1 wherein said gas permeable membrane comprises a hydrophobic membrane having pores of a size smaller than 0.002 mm.

6. A method for measuring the content of a low molecular weight compound in a complex fluid medium, the method comprising the steps of:
conveying said complex fluid medium through a dialyzer;
supplying dialysis fluid to said dialyzer so that it receives a portion of said low molecular weight compound to be measured by diffusion from said complex medium to produce a dialysate;
providing a venting device having a gas permeable membrane which has pores for passing gaseous bubbles therethrough, but which is substantially impervious to the flow of liquid therethrough, said venting device including a fluid inlet and a liquid outlet arranged to be in communication with one side of said gas permeable membrane and a vent arranged to be in communication with the opposite side of said gas permeable membrane in said venting device, said vent being at an elevation above said liquid outlet;
conducting at least a portion of said dialysate into said venting device so that gaseous bubbles in said dialysate pass through said gas permeable membrane to be removed from said portion of said dialysate to provide dialysate with gaseous bubbles removed therefrom;
conducting said dialysate with said gaseous bubbles removed therefrom to said liquid outlet;
arranging a reaction chamber having an inlet relative to said venting device so that said inlet of said reaction chamber is at an elevation below said liquid outlet of said venting device, said reaction chamber containing enzymes for promoting the conversion of a low molecular weight compound to be measured into a converted reaction product; conducting at least a part of said dialysate with said gaseous bubbles removed therefrom into said inlet of said reaction chamber and through said reaction chamber so that said enzymes of said reaction chamber promote the conversion of the low molecular weight compound in said part of said dialysate introduced thereinto into a converted reaction product to provide a processed dialysate; and then conducting said processed dialysate from said reaction chamber to a measuring unit for measuring the concentration of said converted reaction product in said processed dialysate, the concentration of said converted reaction product being representative of the content of said low molecular weight compound in said complex fluid medium.

7. The method of claim 6 further including the step of dividing said dialysate into first and second flows of dialysate prior to the step of conducting at least a portion of said dialysate to a venting device; and wherein the step of conducting at least a portion of said dialysate to said venting device comprises conducting only said first flow of dialysate to said venting device to thereby remove gaseous bubbles from said first flow of dialysate by venting gas bubbles through said vent of said venting device.

8. The method of claim 7 further including the step of conducting said second flow of dialysate directly to said measuring unit to provide a reference measurement for comparison with the measurement of the concentration of said converted reaction product in said processed dialysate from said reaction chamber.

9. The method of claim 8 wherein the step of dividing said dialysate into first and second flows of dialysate comprises intermittently diverting a first part of said dialysate along a first flow path in communication with said venting device for removing gaseous particles while preventing any flow of dialysate along a second flow path which directly communicates with said measuring unit, and then diverting a second part of said dialysate along said second flow path while preventing any flow of dialysate along said first flow path to said venting device.

10. The method of claim 9 further including the step of collecting gaseous bubbles passed through said gas permeable membrane and then discharging said collected gaseous bubbles through said vent of said venting device.

11. The method of claim 10 wherein the step of discharging the collected gaseous particles comprises discharging the collected gaseous particles each time the diversion of said dialysate is intermittently changed.

12. The method of claim 6 further including the step of dividing said dialysate with gaseous bubbles removed therefrom into first and second flows of dialysate after the step venting gaseous bubbles from said at least a portion of said dialysate; and wherein said step of conducting at least a part of said dialysate with gaseous bubbles removed therefrom through said reaction chamber comprises only conducting said first flow of dialysate through said reaction chamber.

13. The method of claim 12 further including the step of conducting said second flow of dialysate directly to said measuring unit to provide a reference measurement for comparison with the measurement of said concentration of said converted reaction product in said processed dialysate.

14. The method of claim 6 wherein said gas permeable membrane comprises a hydrophobic membrane having pores of a size smaller than 0.002 mm.

15. The method of claim 14 wherein said hydrophobic membrane is made from the group consisting of polypropylene teflon and polyethylene.

16. A method of measuring the concentration of a compound in a liquid medium comprising the steps of:
providing a venting device having a gas permeable membrane which has pores for passing gaseous bubbles therethrough, but which is substantially impervious to the flow of liquid therethrough, said venting device further including a fluid inlet and a liquid outlet arranged to be in communication with one side of said gas permeable membrane and a vent arranged to be in communication with the opposite side of said gas permeable membrane in said venting device;

conducting said liquid medium containing said compound whose concentration is to be measured into said inlet of said venting device so that gaseous bubbles in said liquid medium pass through said gas permeable membrane to be removed from said liquid medium;

conducting said liquid medium having said gaseous bubbles removed therefrom from said liquid outlet of said venting device to a reaction chamber, said reaction chamber containing enzymes for promoting the conversion of said compound whose concentration is to be measured into a converted reaction product; and then conducting said liquid medium from said reaction chamber to a measuring unit for measuring the concentration of said converted reaction product in said liquid medium, the concentration of said converted reaction product being representative of the concentration of said compound in said liquid medium.

17. The method of claim 16 wherein said gas permeable membrane comprises a hydrophobic membrane having pores of a size smaller than 0.002 mm.

18. The method of claim 17 wherein said hydrophobic membrane is made from the group consisting of polypropylene, telfon and polyethylene.

19. A method for measuring the content of a low molecular weight compound in a complex fluid medium, the method comprising the steps of:
conveying said complex medium to a dialyzer;
supplying dialysis fluid to said dialyzer so that it receives a portion of the low molecular weight compound to be measured by diffusion from said complex medium to produce a dialysate;
providing a venting device having a gas permeable membrane which has pores for passing gaseous bubbles therethrough, but which is substantially impervious to the flow of liquid therethrough, said venting device including a fluid inlet and a liquid outlet arranged to be in communication with one side of said gas permeable membrane and a vent arranged to be in communication with the opposite side of said gas permeable membrane in said venting device;
conducting at least a portion of said dialysate into said venting device so that gaseous bubbles in said dialysate pass through said gas permeable membrane to be removed from said portion of said dialysate to provide dialysate with gaseous bubbles removed therefrom;

conducting at least a part of said dialysate with gaseous particles removed therefrom through a reaction chamber containing enzymes for promoting the conversion of the low molecular weight compound in said dialysate with gaseous bubbles removed therefrom into a converted reaction product to provide processed dialysate; and then conducting said processed dialysate from said reaction chamber to a measuring unit for measuring the concentration of said converted reaction product in said processed dialysate, the concentration of said converted reaction product being representative of the content of said low molecular weight compound in said complex fluid medium.

20. The method of claim 19 wherein said gas permeable membrane comprises a hydrophobic membrane having pores of a size smaller than 0.002 mm.

21. The method of claim 20 wherein said hydrophobic membrane is made from the group consisting of polypropylene, teflon and polyethylene.

22. Apparatus for measuring the concentration of a compound in a liquid medium comprising:

a fluid conduit through which said liquid medium is conducted;

a venting device disposed in said fluid conduit for removing gaseous bubbles from said liquid medium when said liquid medium is passed therethrough, said venting device including a gas permeable membrane having pores for passing said gaseous bubbles therethrough, but being substantially impervious to the flow of liquid therethrough, said venting device further including an inlet and an outlet arranged relative to said gas permeable membrane to be in communication with one side of said gas permeable membrane and a vent arranged to be in communication with the other side of said gas permeable membrane so that said gaseous bubbles in said liquid medium introduced into said venting device through said inlet pass through said gas permeable membranes to said vent;

a reaction chamber arranged downstream of said venting device to receive said liquid medium with said gaseous bubbles removed therefrom, said reaction chamber including an inlet through which liquid medium is introduced into said reaction chamber and an outlet through which liquid medium is conducted from said reaction chamber, said inlet being at an elevation above said outlet so that said liquid medium is caused to flow downwardly through said reaction chamber, and said inlet of said reaction chamber being disposed at an elevation below said venting device, said reaction chamber containing enzymes for promoting the conversion of said compound whose concentration is to be measured into a converted reaction product; and measurement means arranged downstream of said reaction chamber to receive said liquid medium after passage through said reaction chamber for measuring the concentration of said converted reaction product in said liquid medium when said liquid medium is passed therethrough, the concentration of said converted reaction product being representative of the concentration of said compound in said liquid medium.

23. The apparatus of claim 22 wherein said venting device comprises a housing having said gas permeable membrane therein, said gas permeable membrane dividing said housing into a first chamber and a second chamber, said inlet and said outlet communicating with said first chamber of said housing and said vent communicating with said second chamber of said housing, and said vent positioned at an elevation above said outlet for receiving gaseous bubbles in said liquid medium introduced into said venting device.

24. The apparatus of claim 23 wherein said vent is vented to the atmosphere.

25. The apparatus of claim 23 further including a gas removal conduit communicating with said vent and valve means operative to move between open and closed positions to open and close said gas removal conduit; said valve means being operable to intermittently discharge gaseous bubbles collected in said housing when said valve means is in said closed position.

26. The apparatus of claim 23 wherein said gas permeable membrane comprises a hydrophobic membrane having pores of a size smaller than 0.002 mm.

27. The apparatus of claim 26 wherein said hydrophobic membrane is made from the group consisting of polypropylene, teflon and polyethylene.

28. An apparatus for measuring the content of a low molecular weight compound in a complex fluid medium, comprising:

a dialyzer;

means for conveying said complex fluid medium to said dialyzer;

means for supplying dialysis fluid to said dialyzer so that is receives a portion of the low molecular weight compound by diffusion from said complex fluid medium to produce a dialysate;

flow conducting means for conducting said dialysate from said dialyzer;

a venting device disposed in said fluid conducting means for removing gaseous bubbles from said dialysate when dialysate is passed therethrough, said venting device including a gas permeable membrane having pores for passing said gaseous bubbles therethrough, but being substantially impervious to the flow of liquid therethrough, said venting device further including an inlet and an outlet arranged relative to said gas permeable membrane to be in communication with one side of said gas permeable membrane and a vent arranged to be in communication with the other side of said gas permeable membrane so that said gaseous bubbles in said liquid medium introduced into said venting device through said inlet pass through said gas permeable membranes to said vent;

a reaction chamber arranged downstream of said venting device to receive said dialysate with said gaseous bubbles removed therefrom, said reaction chamber containing enzymes for promoting the conversion of said low molecular weight compound in said dialysate into a converted reaction product to provide processed dialysate, said reaction chamber including an inlet through which said dialysate with said gaseous bubbles removed therefrom is introduced into said reaction chamber and an outlet through which said processed dialysate is conducted from said reaction chamber, said inlet being at an elevation above said outlet so that said dialysate with gaseous bubbles removed therefrom is caused to flow downwardly through said reaction chamber, and said inlet being disposed at an elevation below said venting device; and measurement means arranged downstream of said reaction chamber to receive said processed dialysate after passage through said reaction chamber for measuring the concentration of said converted reaction product in said processed dialysate, the concentration of said converted reaction product being respresentative of the concentration of said low molecular weight compound in said complex fluid medium.

29. The apparatus of claim 28 wherein said venting device comprises a housing having said gas permeable membrane therein, said gas permeable membrane dividing said housing into a first chamber and a second chamber, said inlet and said outlet communicating with said first chamber of said housing and said vent communicating with said second chamber of said housing, said vent being positioned at an elevation above said outlet for receiving gas bubbles in said dialysate introduced into said venting device.

30. The apparatus of claim 29 wherein said vent is vented to the atmosphere.

31. The apparatus of claim 28 wherein said gas permeable membrane comprises a hydrophobic membrane having pores of a size smaller than 0.002 mm.

32. The apparatus of claim 28 further including means for dividing said dialysate into first and second flows of dialysate, said first flow of dialysate being conducted to said reaction chamber and said second flow of dialysate being conducted directly to said measurement means bypassing said reaction chamber so as to provide a reference measurement against which the measurement of said concentration of said converted reaction product may be compared.

33. The apparatus of claim 32 wherein said means for dividing said dialysate into first and second flows includes a shunt flow line communicating with said flow conduit upstream of said reaction chamber and with said measurement means for directing said second flow of said dialysate from a position upstream of said reaction chamber directly to said measurement means, and flow diverting means being movable between a first position and a second position, said flow diverting means when in said first position diverting said dialysate in said flow conduit to flow through said reaction chamber to define said first flow of dialysate and when in said second position diverting said dialysate in said flow conduit to flow through said shunt flow line to bypass said reaction chamber to define said second flow of dialysate.

34. The apparatus of claim 33 wherein said shunt flow line communicates at one end with the downstream side of said gas removal means and at its other end with said measurement means so that said second flow only bypasses said reaction chamber.

35. The apparatus of claim 33 wherein said shunt flow line communicates with said fluid conduit upstream of said venting device so that said second flow of dialysate bypasses both said venting device and said reaction chamber.

36. The apparatus of claim 35 wherein said venting device comprises a housing having said gas permeable membrane disposed therein dividing said housing into a first chamber and a second chamber, said inlet and said outlet communicating with said first chamber of said housing and said vent communicating with said second chamber of said housing, said inlet communicating with said fluid conduit for receiving said first flow of dialysate, said outlet communicating with said reaction chamber and said vent being at an elevation above said outlet.

37. The apparatus of claim 36 further including a gas removal conduit communicating with said vent for receiving gaseous bubbles from said housing, and valve means operable to move between open and closed positions to open and close said gas removal conduit, said valve means being operable to intermittently open said conduit to discharge gaseous bubbles collected in said housing while said valve means is in said closed position.

38. The apparatus of claim 36 further including means for moving said valve means between said open and closed positions in response to said flow diverting means moving between said first and second positions.

39. Apparatus for measuring the concentration of a compound in a liquid medium comprising:
a fluid conduit to which said liquid medium is conducted;
a venting device disposed in said fluid conduit for removing gaseous bubbles from said liquid medium when said liquid medium is passed therethrough, said venting device including a gas permeable membrane having pores for passing said gaseous bubbles therethrough, but being substantially impervious to the flow of liquid therethrough, said venting device further including an inlet and an outlet arranged relative to said gs permeable membrane to be in communication with one side of said gas permeable membrane and a vent arranged to be in communication with the other side of said gas permeable membrane so that gaseous bubbles in said liquid medium introduced into said venting device through said inlet pass through said gas permeable membrane to said vent;
a reaction chamber in fluid communication with said outlet of said venting device for receiving said liquid medium with gaseous bubbles removed therefrom, said reaction chamber containing enzymes for promoting the conversion of said compound whose concentration is to be measured into a converted reaction product; and
measurement means arranged downstream of said reaction chamber so as to receive said liquid medium from said reaction chamber for measuring the concentration of said converted reaction product in said liquid medium when said liquid medium is passed therethrough, the concentration of said converted reaction product being representative of the concentration of said compound in said liquid medium.

40. The apparatus of claim 39 wherein said gas permeable membrane comprises a hydrophobic membrane having pores of a size smaller than 0.002 mm.

41. The apparatus of claim 40 wherein said hydrophobic membrane is made from the group consisting of polypropylene, teflon and polyethylene.

42. Apparatus for measuring the content of a low molecular weight compound in a complex fluid medium, comprising:
a dialyzer;
means for conveying said complex fluid medium through said dialyzer;
means for supplying dialysis fluid to said dialyzer so that it receives a portion of the low molecular weight compound to be measured by diffusion from said complex fluid medium to produce a dialysate;

a venting device arranged to receive at least a portion of said dialysate, said venting device including a gas permeable membrane having pores for passing said gaseous bubbles therethrough, but being substantially impervious to the flow of liquid therethrough, said venting device further including an inlet and an outlet arranged relative to said gas permeable membrane to be in communication with one said of said gas permeable membrane and a vent arranged to be in communication with the other side of said gas permeable membrane so that gaseous bubbles in said portion of said dialysate introduced into said venting device through said inlet pass through said gas permeable membrane to said vent, thereby providing dialysate with gaseous bubbles removed therefrom;

a reaction chamber in fluid communication with said outlet of said venting device for receiving said dialysate with gaseous bubbles removed therefrom, said reaction chamber containing enzymes for promoting the conversion of said low molecular weight compound into a converted reaction product to provide processed dialysate; and measurement means arranged downstream of said reaction chamber to receive processed dialysate from said reaction chamber for measuring the concentration of said converted reaction product in said processed dialysate, the concentration of said converted reaction product being representative of the concentration of said low molecular weight compound in said complex fluid medium.

43. The apparatus of claim 42 wherein said gas permeable membrane comprises a hydrophobic membrane having pores of a size smaller than 0.002 mm.

44. The apparatus of claim 43 wherein said hydrophobic membrane is made from the group consisting of polypropylene, teflon and polyethylene.

* * * * *